United States Patent [19]

Weigel

[11] Patent Number: 5,391,728
[45] Date of Patent: Feb. 21, 1995

[54] BICYCLIC B-LACTAMS INTERMEDIATES HAVING A NEW AMINO PROTECTING GROUP

[75] Inventor: Leland O. Weigel, Indianapolis, Ind.

[73] Assignee: Eli Lilly and Company, Indianapolis, Ind.

[21] Appl. No.: 110,619

[22] Filed: Aug. 23, 1993

Related U.S. Application Data

[60] Division of Ser. No. 25,301, Mar. 2, 1993, Pat. No. 5,283,329, which is a division of Ser. No. 918,916, Jul. 22, 1992, Pat. No. 5,239,069, which is a division of Ser. No. 750,214, Aug. 19, 1991, Pat. No. 5,169,945, which is a continuation of Ser. No. 523,455, May 14, 1990, abandoned.

[51] Int. Cl.⁶ ............................................. C07D 463/00
[52] U.S. Cl. ..................................................... 540/205
[58] Field of Search ......................................... 540/205

[56] References Cited

U.S. PATENT DOCUMENTS

| | | | |
|---|---|---|---|
| 3,905,966 | 9/1975 | Kukolja et al. | 260/243 C |
| 4,085,100 | 4/1978 | Kingsbury | 260/239 A |
| 4,539,152 | 9/1985 | Hashimoto | 540/200 |

OTHER PUBLICATIONS

Wolfe, S. and Hasen, S. K., *Canadian Journal of chemistry*, 48, 3572 (1970).
Osby et al., *Tetrahedron Letters*, vol. 25, No. 20, pp. 2093–2096, 1984.
Gibson, M. S., and Bradshaw, R. W., "The Gabriel Synthesis of Primary Amines", *Angew. Chem. Internat. Edit.*, vol. 7 (1968), No. 12, pp. 919–930.
Kukolja, S., and Lammert, S. R., J.A.C.S., 97:A, 9-1-7-75 (1975).
Kukolja et al., *Croatica Chemica Acta*, 49, (4), pp. 779–795 (1977).
Kume et al., *Tetrahedron Letters*, vol. 23 No. 42 pp. 4365–4368 (1982).
Logusch, E. W., *Tetrahedron Letters*, vol. 27, No. 49, pp. 5935–5948 (1986).
Greene, T. W., *Protective Groups in Organic Synthesis*, New York, John Wiley & Sons, pp. 265–266, (1981).
Uhle, F. C., *J. Org. Chem.*, 26, 2998–3000 (1960).
Kato, *Chem. Abs.*, 70, 114795 (1968).
Ganin, *J. Org. Chem.*, USSR 21, 2205 (1985).
Pastor, *J. Org. Chem.*, 53, 5775 (1988).

*Primary Examiner*—Mark L. Berch
*Attorney, Agent, or Firm*—Paul R. Cantrell; James J. Sales

[57] ABSTRACT

A method for preparing a new class of protected amino intermediates is provided which utilizes reaction of an imido protected primary amine with a secondary amine. The intermediates thus provided are suitably protected for nucleophilic functionalization on the residue of the primary amine. The desired imido protected amine thus derivatized may be regenerated using acid. Further provided are methods for resolving racemic primary amines. Also provided are β-lactam intermediates protected with the new amino protecting group which are useful in the preparation of β-lactam antibiotics.

4 Claims, No Drawings

BICYCLIC B-LACTAMS INTERMEDIATES HAVING A NEW AMINO PROTECTING GROUP

This application is a division of application Ser. No. 08/025,301, filed Mar. 2, 1993, U.S. Pat. No. 5,283,329, which is a division of application Ser. No. 07/918,196, filed Jul. 22, 1992, U.S. Pat. No. 5,239,069, which is a division of application Ser. No. 07/750,214, filed Aug. 19, 1991, U.S. Pat. No. 5,169,945, which is a continuation of application Ser. No. 07/523,455, filed on May 14, 1990 abandoned.

BACKGROUND OF THE INVENTION

The literature is replete with protecting groups suitable for blocking (i.e., protecting) an amino function. For example, see Greene, *Protective Groups in Organic Synthesis*, pp. 218-287, John Wiley & Sons, New York (1980). There are also many examples of protecting groups suitable for protecting an amino function in the presence of the relatively labile β-lactam moiety. The phthalimido group is one such amino protecting group. Kukolja et al., U.S. Pat. No. 3,905,966 teaches the utilization and removal of a 7-phthalimido function of a cephalosporin via a 7-(phthalamic acid) intermediate to provide a 7-amino cephalosporin. The phthalimido group is generally stable to acidic, electrophilic, and oxidative reaction conditions.

However, the base/nucleophile sensitivity of the phthalimido group is well known. S. Wolfe et al., *Canadian J. Chem.*, 1970, 48, 3572-3579 report that hydrolysis of this imide proceeds at pH 7.4 to the phthalamic acid intermediate. Ganem et al., *Tetrahedron Let.*, 1984, 25, 2093-2096 and Uhle, *J. Org. Chem.*, 1960, 26, 2998-3000 report that the phthalimido group reacts readily at ambient temperatures with sodium borohydride. Many synthetic operations, for example, ester hydrolysis, enolate condensations, and alcoholysis reactions are not compatible with the phthalimido group, because such reaction conditions would lead to undesired side-reaction with the phthalimido group. In fact, one preferred method for the removal of a phthalimido group to provide a free primary amine consists of nucleophilic displacement with methyl hydrazine.

In summary, an imido protecting group such as the phthalimido group may be highly desirable in certain circumstances, because the primary amine which it protects is doubly-bonded, thus rendering it stable to a variety of reaction conditions—especially electrophilic or oxidative conditions. However, its instability in the presence of nucleophiles severely circumscribes its utility in synthetic organic chemistry. Thus, the present invention as discussed below provides a solution to this long-standing problem and provides methodology for the synthetic organic chemist to utilize an imido protecting group such as a phthalimido group as an amine-protecting group over a broader spectrum of reaction conditions necessarily encountered in a multi-step synthesis, by reacting said imido group with a secondary amine. The acylamino group which results is stable to nucleophilic conditions. Thus, many desired functional manipulations on the remainder of the molecule may be carried out, and when all such nucleophilic reactions have been completed, the original imido group can be regenerated using acid.

SUMMARY OF THE INVENTION

The present invention provides a process for converting a protected amine of the formula

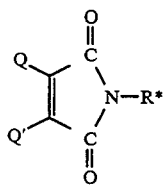

wherein Q and Q' are individually hydrogen, $C_1$-$C_6$ alkyl or when taken together form a divalent radical of the formula —CH=CH—CH=CH—; and R* is an organic residue; to compounds of the formula

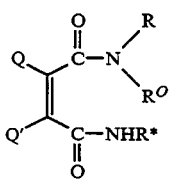

wherein R and $R^0$ are individually $C_1$-$C_6$ alkyl groups or taken together with the nitrogen atom to which they are bonded form an optionally-substituted $C_2$-$C_7$ nitrogen-containing ring, which comprises reacting the imido-protected amine with an amine of the formula $HNRR^0$.

The compounds thus provided may be further derivatized on the R* radical using nucleophilic (especially hydrolytic) reaction conditions generally inappropriate for utilization in the presence of an imido-protected amine. The compounds provided above may then be treated with acid to regenerate the imide shown initially above.

As another aspect of this invention, when the R* residue contains at least one asymmetric center, and thus the imide above is a mixture of enantiomers (i.e., racemic), the present invention provides a method for preparing a diasteromeric mixture by utilizing in the reaction described above, an amine of the formula $HNRR^0$ which contains at least one asymmetric center and exists in optically pure form. The diastereomers thus formed by this reaction may be separated using known methodology, for example, by high performance liquid chromatography. Thus, in a broad sense, a method for "covalent resolution" of a racetalc primary amine of the formula $R*NH_2$ is provided.

The mixture of diastereomers provided above may also be separated as a further aspect of this invention by treatment with acid to provide the imide as described above, because the starting material is a diastereomeric mixture and the individual diastereomers react with acid to reform an imide at different rates; hence, one diastereomer can be converted back to the imide in the presence of the other diastereomer which converts back to the imide much more slowly. In this manner a "kinetic resolution" of a mixture of diastereomeric acyl amines of the formula

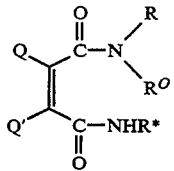

wherein the —NRR⁰ group contains at least one asymmetric center and is optically pure and wherein the R* residue contains at least one asymmetric center and exists as a mixture (i.e., a racemate), can be effected.

Further provided are novel β-lactam intermediates possessing the new amino protecting group as described above, which are useful in the synthesis of β-lactam antibiotics.

DETAILED DESCRIPTION OF THE INVNETION

The present invention provides a process for preparing compounds of Formula (1)

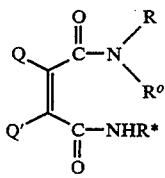

wherein R and R⁰ are individually $C_1$-$C_6$ alkyl groups or with the nitrogen atom to which they are bonded form a $C_2$-$C_7$ nitrogen-containing ring, said ring optionally substituted by one or more $C_1$-$C_6$ alkyl and/or $C_1$-$C_6$ substituted alkyl groups;

Q and Q' are individually hydrogen, $C_1$-$C_6$ alkyl or when taken together form a divalent radical of the formula —CH=CH—CH=CH—; and R* is an organic residue;

which comprises reacting a compound of Formula (2)

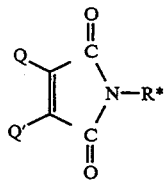

with an amine of the formula HNRR⁰, wherein R, R⁰, Q, Q', and R* are as defined above.

As a further aspect of this invention, there is provided the above process, further comprising the additional steps of
a) subjecting a compound of Formula (1):

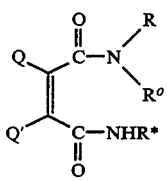

to nucleophilic reaction conditions, followed by b) treatment with acid to provide a compound of Formula (2):

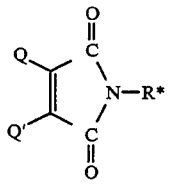

In this aspect of the invention, it will be appreciated that the organic residue R*, can be derivatized to a different R* radical by known methodology utilizing, inter alia, nucleophilic reaction conditions. Thus, when the R* radical of the compound of Formula (1) has been derivatized to a desired end, the imide of Formula (2) may be regenerated by treatment with acid.

As a preferred embodiment of both of the above aspects of the present invention, R* is an organic residue of the formula $$\begin{array}{c} \diagup A \\ \diagdown N_{\diagdown A'} \end{array}$$

wherein A is $C_1$-$C_6$ alkyl, $C_1$-$C_6$ substituted alkyl, —S—($C_1$-$C_6$ alkyl)$CO_2R''$, or —$CH_2$($C_1$-$C_6$ alkyl)-$CO_2R''$, wherein R'' is hydrogen or a carboxy-protecting group;

A' is hydrogen, an amide-protecting group, or a group of the formula —$CH_2CO_2R''$; or A and A' taken together form a group of the formula $$\diagup X \diagdown R^1 \atop CO_2R^2$$

wherein $R^2$ is hydrogen or a carboxy-protecting group; X is sulfur, —$CH_2$—, or oxygen; and $R^1$ is hydrogen, hydroxy, halo, $C_1$-$C_4$ alkoxy, $C_1$-$C_6$ alkyl, $C_1$-$C_6$ substituted alkyl, $C_1$-$C_6$ alkylthio, $C_1$-$C_6$ substituted alkylthio, $C_7$-$C_{12}$ phenylalkyl, $C_7$-$C_{12}$ substituted phenylalkyl, phenyl or substituted phenyl; a group of the formula

—$COR^3$ wherein $R^3$ is hydrogen, $C_1$-$C_6$ alkyl, $C_1$-$C_6$ substituted alkyl, $C_7$-$C_{12}$ phenylalkyl, $C_7$-$C_{12}$ substituted phenylalkyl, phenyl, substituted phenyl, amino, (monosubstituted) amino, or (disubstituted)-amino; a group of the formula

—$COOR^4$ wherein $R^4$ is hydrogen, $C_1$-$C_6$ alkyl, $C_1$-$C_6$ substituted alkyl, $C_7$-$C_{12}$ phenylalkyl, $C_7$-$C_{12}$ substituted phenylalkyl, phenyl, substituted phenyl, or a carboxy-protecting group.

As a further preferred embodiment of both of the above aspects of the present invention, the amine of the formula HNRR⁰ utilized above possesses at least one asymmetric center and exists in optically pure form, thereby providing a compound of the formula

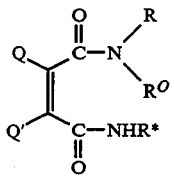

wherein Q, Q', and R* are as described above, and the organic residue, R*, contains at least one asymmetric center and exists as a racemic mixture. The diastereomers provided thereby may be separated using known methodology. For example, since diastereomers, by definition differ in physical properties, they may be separated using any known physical separation method, for example liquid chromatography, preparative thin layer chromatography, or by selective crystallization of one diastereomer. As to the use of the terms diastereomer, racemate, and enantiomer, said terms will be used in their normal context to describe the stereochemistry of discrete compounds of formulae (1) and (2). These terms will also be used to address the stereochemistry of the individual groups —$NRR^0$ and —R* which comprise portions of compounds of the formulae (1) and (2). For example, when the —$NRR^0$ group above is referred to as an enantiomer, or is said to possess at least one asymmetric center in optically pure form, and the —R* group is referred to as a racemate, the discrete compound above will be referred to as a diastereomer.

As a preferred embodiment of this aspect of the invention, R* is an organic residue of the formula

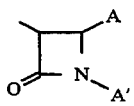

wherein A is $C_1$-$C_6$ alkyl, $C_1$-$C_6$ substituted alkyl, —S—($C_1$-$C_6$ alkyl)$CO_2R''$, or —$CH_2$($C_1$-$C_6$ alkyl)$CO_2R''$, wherein R'' is hydrogen or a carboxy-protecting group; and
A' is hydrogen, an amide-protecting group, or a group of the formula —$CH_2CO_2R''$; or
A and A' taken together form a group of the formula

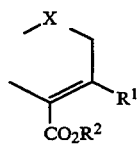

wherein $R^2$ is hydrogen or a carboxy-protecting group; X is sulfur, —$CH_2$—, or oxygen; and $R^1$ is hydrogen, hydroxy, halo, $C_1$-$C_4$ alkoxy, $C_1$-$C_6$ alkyl, $C_1$-$C_6$ substituted alkyl, $C_1$-$C_6$ alkylthio, $C_1$-$C_6$ substituted alkylthio, $C_7$-$C_{12}$ phenyl-alkyl, $C_7$-$C_{12}$ substituted phenylalkyl, phenyl, or substituted phenyl; a group of the formula

—$COR^3$ wherein $R^3$ is hydrogen, $C_1$-$C_6$ alkyl, $C_1$-$C_6$ substituted alkyl, $C_7$-$C_{12}$ phenylalkyl, $C_7$-$C_{12}$ substituted phenylalkyl, phenyl, substituted phenyl, amino, (monosubstituted amino, or (disubstituted)amino; a group of the formula

—$COOR^4$ wherein $R^4$ is hydrogen, $C_1$-$C_6$ alkyl, $C_1$-$C_6$ substituted alkyl, $C_7$-$C_{12}$ phenylalkyl, $C_7$-$C_{12}$ substituted phenylalkyl, phenyl, substituted phenyl, or a carboxy-protecting group.

In a further aspect of the present invention, there is provided a process for preparing compounds of the formulae

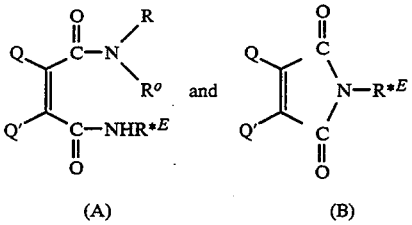

wherein Q and Q' are individually hydrogen, $C_1$-$C_6$ alkyl, or when taken together form a divalent radical of the formula —CH=CH—CH=CH—; R and $R^0$ are individually $C_1$-$C_6$ alkyl groups or with the nitrogen atom to which they are bonded form a $C_2$-$C_7$ nitrogen containing ring, said ring optionally substituted by one or more $C_1$-$C_6$ alkyl and/or $C_1$-$C_6$ substituted alkyl groups; said R and $R^0$ groups together possessing a sum of at least one asymmetric center in optically pure form; $R^{*E}$ is an organic residue containing at least one asymmetric center, said organic residue in optically pure form; which comprises reacting a compound of the formula

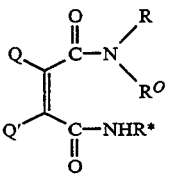

with acid, wherein R and $R^0$ are as defined above; and wherein R* is an organic residue $R^{*E}$ as defined above, however in racemic form; followed by separating compound (A) from compound (B). It will be appreciated by one of ordinary skill in the art that the reaction depicted above provides a mixture of products which is enhanced in enantiomeric purity of the starting material of one isomer and the ring-closed or imido form of the corresponding opposite isomer relative to the racemic starting material. Thus, since the diastereomers react with acid at different rates, (i.e., each possesses different reaction kinetics), enantiomerically enhanced solutions of one enantiomer can be generated by monitoring the reaction mixture and isolating the desired product at the appropriate point to maximize yield and optical purity. Thus, because the component diastereomers of the formula

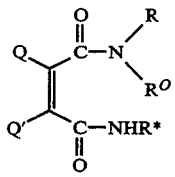

react with acid at different rates, a "kinetic resolution" of one imido diastereomer can be effected. Since one acyl-protected diastereomer converts back to its corresponding imido form at a faster rate, the two products can be differentiated and either crystallized out of solution selectively or separated by physical methods. While one diastereomer reacts with acid to form the imido derivative, the other diastereomer also reacts, but at a slower rate, and if the kinetics of the reaction are monitored and isolation carried out accordingly, one can obtain an imido or acyl protected compound of either formula above which is enhanced in enantiomeric or diastereomeric purity, respectively.

As a preferred embodiment of the above aspect of the present invention R* is a racemic mixture of the formulae

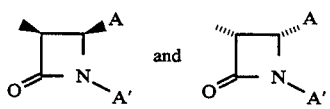

wherein A is $C_1$-$C_6$ alkyl, $C_1$-$C_6$ substituted alkyl, —S—($C_1$-$C_6$ alkyl)$CO_2R''$ or —$CH_2$($C_1$-$C_6$ alkyl)-$CO_2R''$, wherein $R''$ is hydrogen or a carboxy-protecting group; A' is hydrogen, an amide-protecting group, or a group of the formula —$CH_2CO_2R''$; or A and A' taken together form a group of the formula

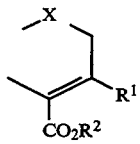

wherein $R^2$ is hydrogen or a carboxy-protecting group; X is sulfur, —$CH_2$—, or oxygen; and $R^1$ is hydrogen, hydroxy, halo, $C_1$-$C_4$ alkoxy, $C_1$-$C_6$ alkyl, $C_1$-$C_6$ substituted alkyl, $C_1$-$C_6$ alkylthio, $C_1$-$C_6$ substituted alkylthio, $C_7$-$C_{12}$ phenylalkyl, $C_7$-$C_{12}$ substituted phenylalkyl, phenyl or substituted phenyl; a group of the formula

—$COR^3$ wherein $R^3$ is hydrogen, $C_1$-$C_6$ alkyl, $C_1$-$C_6$ substituted alkyl, $C_7$-$C_{12}$ phenylalkyl, $C_7$-$C_{12}$ substituted phenylalkyl, phenyl, substituted phenyl, amino, (monosubstituted) amino, or (disubstituted)-amino; a group of the formula

—$COOR^4$ wherein $R^4$ is hydrogen, $C_1$-$C_6$ alkyl, $C_1$-$C_6$ substituted alkyl, $C_7$-$C_{12}$ phenylalkyl, $C_7$-$C_{12}$ substituted phenylalkyl, phenyl, substituted phenyl, or a carboxy-protecting group.

In the above formulae, the term "organic residue" (R*) refers to any hydrocarbyl radical optionally substituted with any variety of functional groupings not limited to those discussed herein. In this regard, one of ordinary skill in the art of synthetic organic chemistry will appreciate that the invention herein expands the utility of imido protecting groups, preferably the phthalimido group, in conjunction with synthetic manipulations on a substrate of the formula R*$NH_2$. One of ordinary skill will appreciate that the R* radical can be literally any residue of a primary amine R* $NH_2$. For example, R*$NH_2$ can be a 6-amino penicillinic acid, a 7-amino-3-cephem, a 7-amino 1-carba(1-dethia)cephem, a 6-amino-penam, a 3-amino monocyclic β-lactam or a 7-amino-1-oxo(1-dethia)cephem. Further, R* may be a residue of a macrolide or tetracycline antibiotic, a steroid, or a leukotriene. Thus, the identity of R* is not crucial so long as it represents an organic residue upon which one or more synthetic manipulations, including nucleophilic reactions may be desired.

The term "$C_1$-$C_6$ alkyl" denotes such groups as methyl, ethyl, n-propyl, iso-propyl, n-butyl, sec-butyl, tert-butyl, amyl, tert-amyl, hexyl and the like. The preferred "$C_1$-$C_6$ alkyl" group is methyl.

The term "$C_1$-$C_6$ substituted alkyl" denotes the above $C_1$-$C_6$ alkyl groups having one or two substituents selected from halogen, hydroxy, protected hydroxy, amino, protected amino, $C_1$-$C_7$ acyloxy, nitro, carboxy, protected carboxy, carbamoyl, carbamoyloxy, cyano, methylsulfonylamino or $C_1$-$C_4$ alkoxy groups.

Examples of the above substituted alkyl groups are the cyanomethyl, nitromethyl, hydroxymethyl, trityloxymethyl, propionyloxymethyl, aminomethyl, carboxymethyl, allyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, 6-hydroxyhexyl, 2,4-dichloro(n-butyl), 2-amino(iso-propyl), 2-carbamoyloxyethyl and the like. A preferred group of examples within the above "$C_1$-$C_6$ substituted alkyl" group are the substituted methyl group, e.g., a methyl group substituted by the same substituents as the "$C_1$ to $C_6$ substituted alkyl" group. Examples of the substituted methyl group include groups such as hydroxymethyl, protected hydroxymethyl, (e.g., tetrahydropyranyloxymethyl), acetoxymethyl, carbamoyloxymethyl, chloromethyl, bromomethyl and iodomethyl.

The term "$C_1$-$C_4$ alkoxy" as used herein denotes groups such as methoxy, ethoxy, n-propoxy, iso-propoxy, n-butoxy, t-butoxy and like groups. The term "$C_1$-$C_7$ acyloxy" denotes herein groups such as formyloxy, acetoxy, propionyloxy, butyryloxy, pentanoyloxy, hexanoyloxy, heptanoyloxy, and the like. Similarly, the term "$C_1$-$C_7$ acyl" encompasses groups such as formyl, acetyl, propionyl, butyryl, pentanoyl, hexanoyl, heptanoyl, benzoyl and the like.

The term "substituted phenyl" specifies a phenyl group substituted with one or two moieties chosen from the group consisting of halogen, hydroxy, protected hydroxy, cyano, nitro, $C_1$-$C_6$ alkyl, $C_1$-$C_4$ alkoxy, carboxy, protected carboxy, carboxymethyl, protected carboxymethyl, hydroxymethyl, protected hydroxymethyl, aminomethyl, protected aminomethyl, trifluoromethyl or N-(methylsulfonylamino).

Examples of the term "substituted phenyl" are a mono- or di(halo)phenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4- fluorophenyl, 2-fluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a monoor di(lower alkyl)-phenyl group such as 4-methylphenyl, 2,4-dimethylphenyl, 2-methylphenyl, 4-(iso-propyl)phenyl, 4-ethylphenyl, 3-(n-propyl)phenyl and the like; a mono-or di(alkoxy)phenyl group, for example, 2,6-dimethoxyphenyl, 4-methoxyphenyl, 3-ethoxyphenyl, 4-(iso-propoxy)-phenyl, 4-(t-butoxy)phenyl, 3-ethoxy-4-methoxyphenyl and the like; 3- or 4- trifluoromethylphenyl; a mono- or dicarboxyphenyl or (protected carboxy)phenyl group such as 4-carboxyphenyl or 2,4-di(protected carboxy)-phenyl; a mono- or di(hydroxymethyl)phenyl or (protected hydroxymethyl)phenyl such as 3-(protected hydroxymethyl)phenyl or 3,4-di(hydroxymethyl)phenyl; a mono- or di(aminomethyl)-phenyl or (protected aminomethyl)phenyl such as 2-(aminomethyl)phenyl or 2,4-(protected aminomethyl)phenyl; or a mono- or di(N-(methylsulfonylamino))phenyl such as 3-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and the like. Preferred substituted phenyl groups include the 2- and 3-trifluoromethylphenyl, the 4-hydroxyphenyl, the 2-aminomethylphenyl and the 3-(N-(methylsulfonylamino))phenyl groups.

The terms "halo" and "halogen" refer to the fluoro, chloro, bromo or iodo groups. Chloro is preferred.

The terms $C_1$-$C_6$ alkylthio and $C_1$-$C_6$ substituted alkylthio denote $C_1$-$C_6$ alkyl and $C_1$-$C_6$ substituted alkyl groups, respectively, attached to a sulfur which is in turn the point of attachment for the $C_1$-$C_6$ alkylthio or $C_1$-$C_6$ substituted alkylthio group.

The term "$C_7$-$C_{12}$ phenylalkyl" denotes a $C_1$-$C_6$ alkyl group substituted at any position by a phenyl ring. Examples of such a group include phenyl methyl (benzyl), 2-phenylethyl, 3 -phenyl- ( n-propyl ), 4-phenylhexyl, 3-phenyl-(n-amyl ), 3-phenyl-(sec-butyl ), and the like. A preferred group is the benzyl group.

The term "$C_7$-$C_{12}$ substituted phenylalkyl" denotes a $C_7$-$C_{12}$ phenylalkyl group substituted on the $C_1$-$C_6$ alkyl portion with one or two groups chosen from halogen, hydroxy, protected hydroxy, amino, protected amino, $C_1$-$C_6$ acyloxy, nitro, carboxy, protected carboxy, carbamoyl, carbamoyloxy, cyano, $C_1$-$C_6$ alkylthio, N-(methylsulfonylamino) or $C_1$-$C_4$ alkoxy; and/or the phenyl group may be substituted with 1 or 2 groups chosen from halogen, hydroxy, protected hydroxy, nitro, $C_1$-$C_6$ alkyl, $C_1$-$C_4$ alkoxy, carboxy, protected carboxy, carboxymethyl, protected carboxymethyl, hydroxymethyl, protected hydroxymethyl, aminomethyl, protected aminomethyl, or an N-(methylsulfonylamino) group. As before, when either the $C_1$-$C_6$ alkyl portion or the phenyl portion or both are disubstituted, the substituents can be the same or different.

Examples of the term "$C_7$-$C_{12}$ substituted phenyl alkyl" are groups such as 2-phenyl-l-chloroethyl, 2-(4-methoxyphenyl)ethyl, 2,6-dihydroxy-4-phenyl (n-hexyl), 5-cyano-3-methoxy-2-phenyl (n-pentyl), 3-(2,6-dimethylphenyl) n-propyl, 4-chloro-3-aminobenzyl, 6-(4-methoxyphenyl)-3-carboxy(n-hexyl), 5-(4-aminomethyl phenyl)-3-(aminomethyl)(n-pentyl), and the like.

The term "(monosubstituted)amino" refers to an amino group with one substituent chosen from the group consisting of phenyl, substituted phenyl, $C_1$-$C_6$ alkyl, and $C_7$-$C_{12}$ phenylalkyl, wherein the latter three substituent terms are as defined above.

The term "(disubstituted)amino" refers to amino groups with two substituents chosen from the group consisting of phenyl, substituted phenyl, $C_1$-$C_6$ alkyl, and $C_7$-$C_2$ phenylalkyl wherein the latter three substituent terms are as described above. The two substituents can be the same or different.

The term "carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2', 4,4'-tetramethoxybenzhydryl, t-butyl, t-amyl, trityl, 4-methoxytrityl, 4,4'-dimethoxytrityl, 4,4',4''-trimethoxytrityl, 2-phenylprop-2-yl, trimethylsilyl, t-butyldimethylsilyl, phenacyl, 2,2,2-trichloroethyl, β-(trimethylsilyl)ethyl, β-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. The species of carboxy-protecting group employed is not critical so long as the derivatized carboxylic acid is stable to the condition of subsequent reaction(s) on other positions of the molecule and can be removed at the appropriate point without disrupting the remainder of the molecule. Preferred carboxylic acid protecting groups are the allyl and p-nitrobenzyl groups. Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5. A related term is "protected carboxy", which refers to a carboxy group substituted with one of the above carboxy-protecting groups.

As used herein, the term "amide-protecting group" refers to any group typically used in the β-lactam art for protecting the β-lactam ring nitrogen from undesirable side reactions. Such groups include p-methoxyphenyl, 3,4-dimethoxybenzyl, benzyl, O-nitrobenzyl, di-(p-methoxyphenyl)methyl, triphenylmethyl, (p-methoxyphenyl)diphenylmethyl, diphenyl-4-pyridylmethyl, m-2-(picolyl)-N'-oxide, 5-dibenzosuberyl, trimethylsilyl, t-butyl dimethylsilyl, and the like. Further descriptions of protecting groups denoted by this term can be found in "Protective Groups in Organic Synthesis", by Theodora W. Greene, 1981, John Wiley & Sons, New York.

In the amine of formula $HNRR^0$, as defined above, one of ordinary skill will appreciate that the R and $R^0$ groups should be chosen in order to provide an amine of sufficient nucleophilic character. In other words, if R and $R^0$ are relatively large or bulky groups, the amine of formula $HNRR^0$ could be significantly sterically hindered and thus nonreactive with the carbonyl moiety of compounds of Formula (2). Examples of useful amines of the formula $HNRR^0$ are aziridine, azetidine, pyrrolidine, piperidine, dimethylamine, diethylamine, dipropylamine, dibutylamine, dipentylamine, dihexylamine, dihextylamine, methyl hexylamine, ethyl hexylamine and the like. Further, one of ordinary skill will appreciate that this amine may be used as a reagent in homogeneous form, or may be covalently immobilized on a solid support matrix using known methodology.

A further preferred group of amines of the formula HNRR⁰ are those which possess at least one asymmetric center and are in optically pure form. Accordingly, when an optically active compound of the formula HNRR⁰ is reacted with a compound of Formula (2), the resulting compound of Formula (1) will exist as a mixture of diastereomers, which, consequently differ in physical and chemical properties. This difference in physical properties allows the component diastereomers to be separated by known physical separation methods such as liquid chromatography, preparative thin layer chromatography, or by selective crystallization of one isomer away from the other. The difference in chemical properties exhibits itself in the relative reactivity that the diastereomers of Formula (1) react with acid.

As described herein, compounds of Formula (1) can be converted back to a compound of Formula (2) by treatment with acid. In this aspect of the process, the term "acid" refers to any strong mineral acid, for example, HCl.

A B(OH)₃/HF mixture in tetrahydrofuran/water is preferred although it was found that B(OH)₃ and HF individually did not effect the conversion of the acyl derivative back to the imido protected form.

Amines of the formula HNRR⁰ that possess an asymmetric center are readily identified by one of ordinary skill in organic chemistry. Illustrative of such amines are the following: 2-chloropropylamine, 2-methyl azetidine, methyl-(2-methyl)propylamine, 2-methyl pyrrolidine, 3-amino-pentyne, 2-cyclopropyl ethylamine, methylbenzylamine, 2-methoxymethyl pyrrolidine and 2-carboxamido-3-pyrrolidine.

In the above process suitable solvents include, in general, polar or apolar, non-protic, non-amino-reactive, non-basic, non acidic reagents, for example, acetonitrile, tetrahydrofuran, N,N-dimethylformamide, or dimethylsulfoxide. Methanol, water, and CH₂Cl₂ were found to be unsuitable in the above process.

The above process is ideally carried out at a temperature from about 0° C. to about 70°–80° C., depending upon the reactivity of the amine (HNRR⁰) and the particular imido substrate of Formula (2).

As an illustration of how the process of the present invention can be utilized, scheme below sets forth a sequence useful for the total synthesis of 1-carba(dethia)-3-cephems. Further provided below are novel intermediates utilizing the new protecting group taught herein.

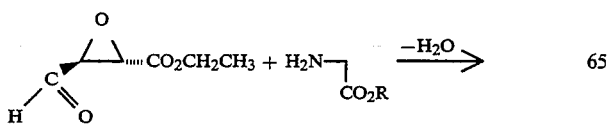

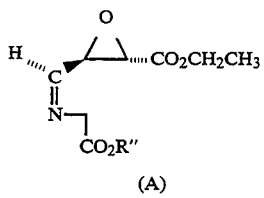

(A)

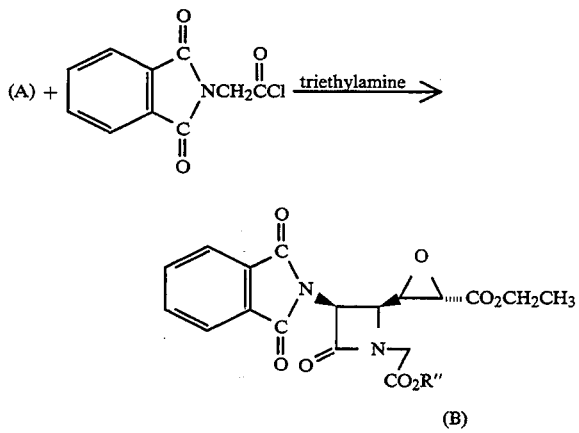

(B)

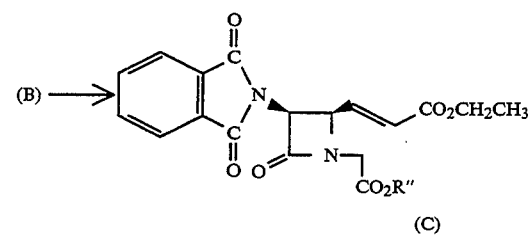

(C)

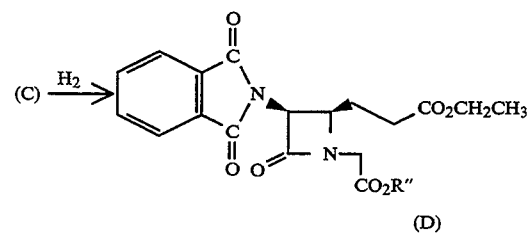

(D)

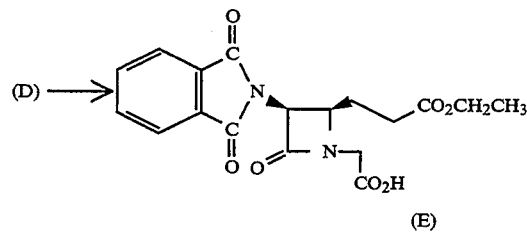

(E)

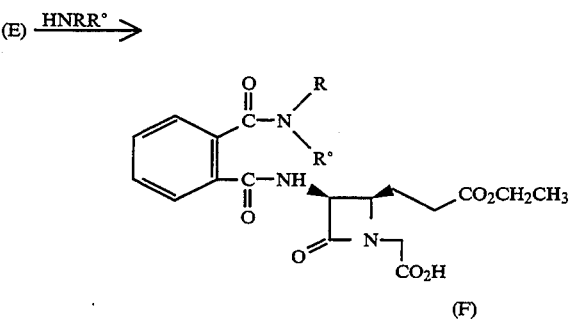

(F)

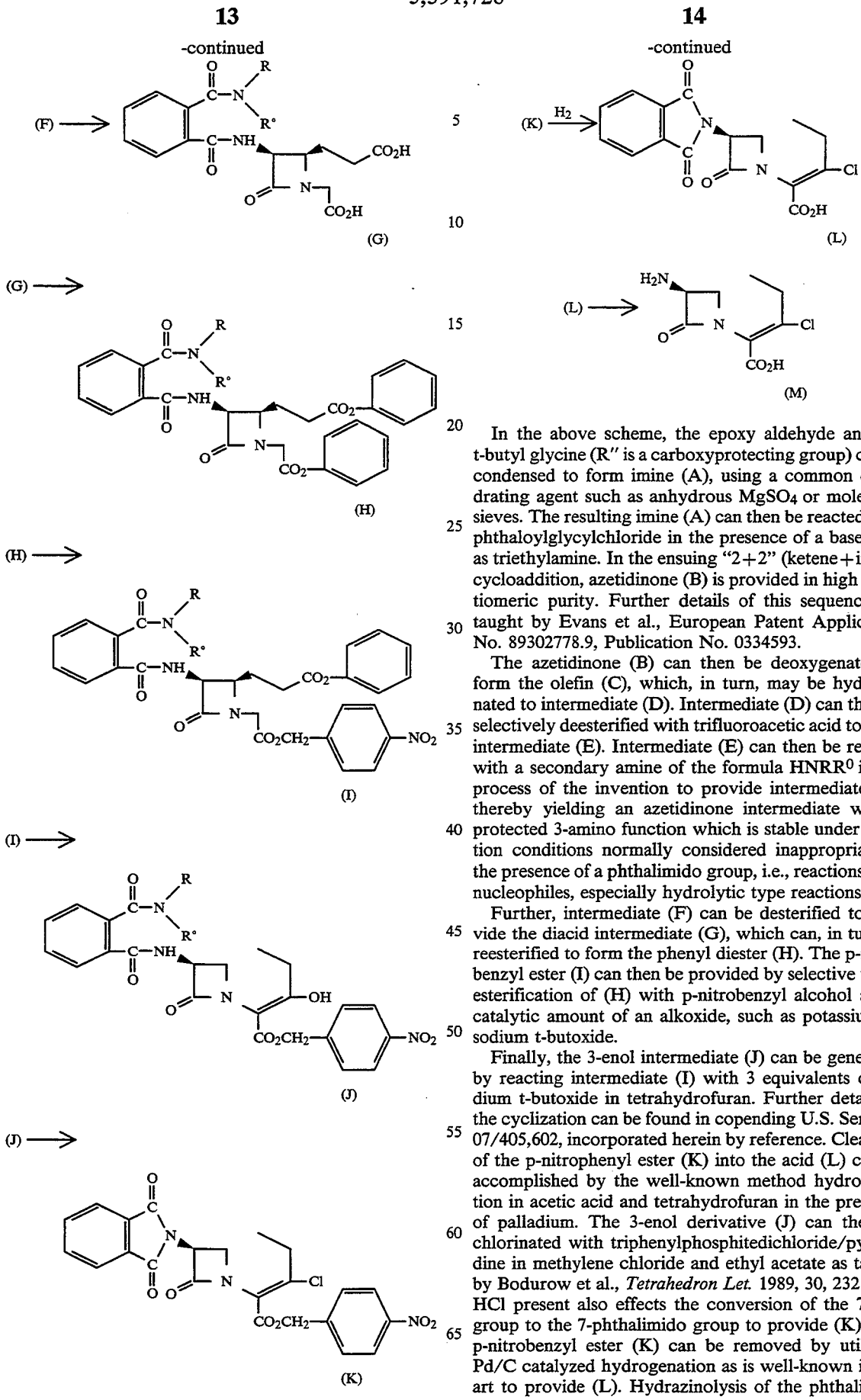

In the above scheme, the epoxy aldehyde and the t-butyl glycine (R" is a carboxyprotecting group) can be condensed to form imine (A), using a common dehydrating agent such as anhydrous $MgSO_4$ or molecular sieves. The resulting imine (A) can then be reacted with phthaloylglycylchloride in the presence of a base such as triethylamine. In the ensuing "2+2" (ketene+imine) cycloaddition, azetidinone (B) is provided in high enantiomeric purity. Further details of this sequence are taught by Evans et al., European Patent Application No. 89302778.9, Publication No. 0334593.

The azetidinone (B) can then be deoxygenated to form the olefin (C), which, in turn, may be hydrogenated to intermediate (D). Intermediate (D) can then be selectively deesterified with trifluoroacetic acid to yield intermediate (E). Intermediate (E) can then be reacted with a secondary amine of the formula $HNRR^0$ in the process of the invention to provide intermediate (F), thereby yielding an azetidinone intermediate with a protected 3-amino function which is stable under reaction conditions normally considered inappropriate in the presence of a phthalimido group, i.e., reactions with nucleophiles, especially hydrolytic type reactions, Further, intermediate (F) can be desterified to provide the diacid intermediate (G), which can, in turn be reesterified to form the phenyl diester (H). The p-nitrobenzyl ester (I) can then be provided by selective transesterification of (H) with p-nitrobenzyl alcohol and a catalytic amount of an alkoxide, such as potassium or sodium t-butoxide.

Finally, the 3-enol intermediate (J) can be generated by reacting intermediate (I) with 3 equivalents of sodium t-butoxide in tetrahydrofuran. Further details of the cyclization can be found in copending U.S. Ser. No. 07/405,602, incorporated herein by reference. Cleavage of the p-nitrophenyl ester (K) into the acid (L) can be accomplished by the well-known method hydrogenation in acetic acid and tetrahydrofuran in the presence of palladium. The 3-enol derivative (J) can then be chlorinated with triphenylphosphitedichloride/pyrimidine in methylene chloride and ethyl acetate as taught by Bodurow et al., *Tetrahedron Let.* 1989, 30, 2321; the HCl present also effects the conversion of the 7-acyl group to the 7-phthalimido group to provide (K). The p-nitrobenzyl ester (K) can be removed by utilizing Pd/C catalyzed hydrogenation as is well-known in the art to provide (L). Hydrazinolysis of the phthalimido intermediate (L) into (M) has been reported by Hirata et al., *Chem. Pharm. Bull. Jap.* 1989, 37, 1239.

The resulting 7-β-amino-1-carba(dethia)-3-chloro-3-cephem-4-carboxylic acid (M) can then be acylated with an activated form of phenylglycine using known methodology to provide the antibiotic, loracarbef, 7-β-(D-phenyl-glycylamido)-1-carba(dethia)-3-chloro-3-cephem-4-carboxylic acid. Further details of these manipulations may be found in U.S. Pat. No. 4,708,956, incorporated herein by reference.

As a further aspect of the invention, there are provided compounds of the formula

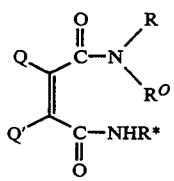

wherein R* is a group of the formula

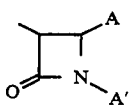

wherein

R and $R^0$ are individually $C_1$-$C_6$ alkyl groups or with the nitrogen atom to which they are bonded form a $C_2$-$C_7$ nitrogen-containing ring, said ring optionally substituted by one or more $C_1$-$C_6$ alkyl and/or $C_1$-$C_6$ substituted alkyl groups;

Q and Q' are individually hydrogen, $C_1$-$C_6$ alkyl, or when taken together form a divalent radical of the formula —CH=CH—CH=CH—;

A is $C_1$-$C_6$ alkyl, $C_1$-$C_6$ substituted alkyl, —S—($C_1$-$C_6$alkyl)$CO_2R''$, or —$CH_2$($C_1$-$C_6$alkyl)$CO_2R''$ wherein R" is hydrogen or a carboxy-protecting group;

A' is hydrogen, an amide-protecting group, or a group of the formula —$CH_2CO_2R''$; or A and A' taken together form a group of the formula

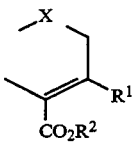

wherein $R^2$ is hydrogen or a carboxy-protecting group; X is sulfur, —$CH_2$—, or oxygen;

$R^1$ is hydrogen, hydroxy, halo, $C_1$-$C_6$ alkoxy, $C_1$-$C_6$ alkyl, $C_1$-$C_6$ substituted alkyl, $C_1$-$C_6$ alkylthio, $C_1$-$C_6$ substituted alkylthio, $C_7$-$C_{12}$ phenylalkyl, $C_7$-$C_{12}$ substituted phenylalkyl, phenyl or substituted phenyl; a group of the formula

—$COR^3$ wherein $R^3$ is hydrogen, $C_1$-$C_6$ alkyl, $C_1$-$C_6$ substituted alkyl, $C_7$-$C_{12}$ phenylalkyl, $C_7$-$C_{12}$ substituted phenylalkyl, phenyl, substituted phenyl, amino, (monosubstituted)-amino, or (disubstituted)- amino; a group of the formula

—$COOR^4$ wherein $R^4$ is hydrogen, $C_1$-$C_6$ alkyl, $C_1$-$C_6$ substituted alkyl, $C_7$-$C_{12}$ phenylalkyl, $C_7$-$C_{12}$ substituted phenylalkyl, phenyl, substituted phenyl, or a carboxy-protecting group.

As a further aspect of the present invention, there are provided novel compounds F, G, H, I and J as depicted in the scheme above which utilize the new protecting group taught herein and are useful in preparing the β-lactam antibiotic, loracarbef. A preferred aspect of this aspect of the invention is the above group of compounds in which R and $R^0$ are taken together and, along with the nitrogen atom to which they are attached form a pyrrolidino ring. Phthalimido-protected intermediates C, D, and E, above, are also provided as a further aspect of the invention and are useful in preparing intermediate F as well as expanding the utility of the Evans chiral epoxide methodology referred to in step 1 of the above scheme, since by virtue of the discovery of the present invention, a phthalimido group may be used in the beginning stages of the above scheme, then converted to the new acyl protecting group before the nucleophilic cyclization to (J), and then converted back to a phthalimido-protected intermediate (K). Thus, the present invention allows one to use the highly desirable phthalimido group in the cycloaddition, and avoid complete removal of the phthalimido group, followed by reprotection with a different protecting group that would be stable under the conditions providing intermediate (J).

EXPERIMENTAL SECTION

Preparation 1

(2-ethoxycarbonyl)-(1-formyl)ethylene oxide

The procedure described by Evans and Williams European Patent Application No. 89302778.9, Publication No. 0334593 was employed for the Swern oxidation of (2-ethoxycarbonyl)-(1-hydroxymethyl) ethylene oxide (5.00 g) in methylene chloride (total 170 ml) with dimethylsulfoxide (7.3 mL), oxalyl chloride (4.2 mL) and triethylamine. Extractive work-up involving brine (150 mL), followed by trituration of impurities with pentane-ethyl acetate (2:1, 450 mL) afforded the title aldehyde (4.0 g, 80%). This material is used immediately and/or stored in dry methylene chloride at −25° C. under nitrogen.

TLC: Rf, 0.49 (ethyl acetate-petroleum ether, 1:1).

$^1$H NMR (CDCl$_3$):δ 1.30 (t,J=7.2, 3H), 3.59 (dxd, J=1.5 and 6.4, 1H), 3.73 (d, J=1.5, 1H), 4.26 (m, 2H), 9.03 (d, J=6.4, 1H).

Reaction with 2,4-dinitrophenylhydrazone produced a compound with MS (FD) m/z =324.

Example 1

1-t-butoxycarbonyl-3-β-phthaloylamino-4β-(2-ethoxycarbonyl)ethylene oxide-1-yl-azetidin-2-one The process described by Evans, European Patent Application No. 89302778.9 was employed to convert the unstable epoxide from Preparation 1 (4.5 g in 167 mL of methylene chloride) into the intermediate imine with t-butylglycinate (45 mL of a 0.684M solution in methylene chloride) using 4Å molecular sieves (25g, 0°, 1 h). Immediate reaction of this imine solution with phthalimidoacetylchloride (6.97 g in 100 mL of methylene chloride) and triethylamine (4.74 g; −78° C. for 15 minutes then −20° C. for 18 hr) followed by extractive work-up (water and sodium bicarbonate) and recrystallization from ethyl acetate-hexane afforded the title compound (6.50 g) as colorless needles.
IR (CHCl$_3$): 1782.7, 1775, 1726.9 cm$^{-1}$.
mp. 187.5°–189° C.
TLC: Rf, 0.45 (diethylether).
Elem. Analysis Calculated for C$_{22}$H$_{24}$N$_2$O$_8$ C, 59.46; H, 5.44; N 6.30. Found: C, 59.62; H, 5.44; N, 6.25
$^1$H NMR (CDCl$_3$):δ7.87 (m, 2H), 7.78 (m 2H), 5.63 (d, 1H), 4.13 (dxd, 2H), 3.90 (m, 2H), 3.63 (m, 1H) 3.51 (dxd, 1H), 3.16 (d, 1H), 151 (s, 9H), 0.83 (t, 3H)
Diastereomeric purity was established by examination of the $^1$H NMR (500 MHz) in CDCl$_3$ and DMSO-d$_6$ in the presence of europium Opti-shift ®, 2,2,2-trifluoroanthrylethanol, and mandelic acid. No peak doubling was seen in any of the above experiments.
$^{13}$C NMR(CDCl$_3$): δ14.59, 29.05, 44.56, 56.18, 57.43, 61.94, 62.57, 84.19, 124.85, 132.51, 135.72, 164.77, 167.46, 167.95, 168.08.

Example 2

1-t-Butoxycarbonylmethyl-3-β-phthaloylamino-4β-(2-ethoxycarbonyl) ethene-1-yl-azetidin-2-one The epoxide from Example 1 (7.25 g) in acetonitrile (100 mL) was treated with sodium iodide (4.9 equiv.) and then p-toluenesulfic acid (12.5 g in acetonitrile added at 3° C. over 2 h). Extractive work-up involving ethyl acetate (800 mL), saturated aqueous sodium bicarbonate (100 mL), aqueous sodium thiosulfate (10%, 4×100 mL), brine (100 mL), and sodium sulfate (as a drying agent) provided the unsaturated ester (white foam, 6.55 g, 94%) after evaporation of the dried extracts.
TLC: Rf, 0.5 ( one spot, ethyl acetate-hexane, 1:1)
$[\alpha]_{589}$=+34.17° (C=1, MeOH)
$[\alpha]_{365}$=+85.32° (C=1, MeOH)
Analysis: Calculated for C$_{22}$H$_{24}$N$_2$O$_7$ Calc.: C, 61.68; H, 5.65; N, 6.54; Found: C, 60.70; H, 5.20; N, 6.28.
$^{13}$C NMR (CDCl$_3$): 6 14.06, 28.08, 43.00, 58.75, 59.70, 60.72, 83.09, 123.88, 128.08, 131.54, 134.59, 134.66, 139.88, 163.83,164.79, 166.66, 166.93.
$^1$H NMR (CDCl$_3$): δ7.87 (m, 2H), 7.83 (m, 2H), 6.87 (dxd, 1H), 6.10 (dxd, 1H), 5.67 (d, 1H), 4.84 (dxd, 1H), 4.38 (d, 1H), 4.10 (q, 2H), 3.69 (d, 1H), 1.47 (s, 9H), 1.18 (t, 3H).

Example 3

1-t-Butoxycarbonylmethyl-3β-phthaloylamino-4β-(2-ethoxycarbonyl)ethan-1-yl

The unsaturated ester from Example 2 (0.5 g) was hydrogenated, (1 atm. hydrogen, 25° C., 2.5 h) with palladium on carbon (5% w/w, 0.5 g) in ethanol after which the solution was filtered and evaporated to provide the title compound as a foam 0 465 g 93% MS (FD) m/z =430.
$^1$H NMR (CDCl$_3$):δ 7.87 (m, 2H), 7.75 (m, 2H), 5.51 (d, 1H), 4.06 (q, 2H), 1.49 (s, 9H), 1.17 (t,3H).
$^{13}$C NMR (CDCl$_3$):δ 171.95, 167.37, 166.78, 135.69

Example 4

1-t-butoxycarbonylmethyl-3β-(2-pyrrolidinecarbonyl) benzoylamino-4β- (2-ethoxycarbonyl)ethan-1-yl-azetldin-2-one Reaction of pyrrolidine (0.016 mL) with the phthalimide from Example 3 (69.3 mg) in tetrahydrofuran (0.20 mL; 25° C., 2 h) provided the title compound as a white foam, 79 mg, 98%.
HPLC (Zorbax ® C-8,254 nm) 98% integration TLC: Rf, 0.21 (ethyl acetate-hexane, 2:1).

Example 5

1-t-Butoxycarbonylmethyl-3β-(2-pyrrolidinocarbonyl)-benzoylamino-4β-(2-ethoxycarbonyl)ethylene oxide-1-yl-azetidin-2-one Reaction of a (200 mg) sample of the material from Example 1 in tetrahydrofuran (3.0 mL) with pyrrolidine (40 μL, 25° C., 3 h) afforded the 228 mg of the title compound as a foam after evaporation of the solvent and vacuum drying.
TLC: Rf, 0.67 (ethyl acetate-hexane-methanol, 1:1:1).
Analysis Calculated for C$_{22}$H$_{24}$N$_2$O$_8$N$_9$: Calc.: C, 60.57; H, 6.45; N, 8.15; Found: C, 60.80; H, 6.44; N, 7.91.
MS (FD)m/z=515 (100%).
$^1$H NMR (DMSO-d$_6$) :δ9.33 (d, 1H), 7.40–7.60 (m, 3H), 7.31 (d, 1H), 5.35 (dxd, 1H), 4.08 (m, 1H), 4.04 (dxd, 2H), 3.87 (m, 1H), 3.60 (m, 1H), 3.08 (dxd, 2H), 1.82 (m, 4H), 1.47 (s, 9H), 0.94 (t, 3H).

Example 6

Sodium 1-t-butoxycarbonyl-3- ( 2-pyrrolidinocarbonyl) benzoylamino-4β-(2-carboxylate )ethylene oxide-1yl-azetidine-2-one To the compound of Example 5 (46.0 mg) in tetrahydrofuran-acetonitrile-dimethyl sulfoxide (1 mL, 7:7:1) was added a solution of sodium hydroxide (1N, 0,089 mL, 25° C.) in six portions over 2 h. All of the solvent was removed in a stream of nitrogen and the residue dried under high vacuum affording the title compound as a foam. Yield:
TLC: Rf, 0.18 (methanol-ethyl acetate-hexane, 2:1:1)
HPLC (Zorbax ® C-8, 254 nm) >95% integration.
$^1$HNMR (DMSO-d6):δ 9.20 (d, 1H), 7.50 (d, 1H), 7.52 (m, 1H), 7.43 (m, 1H), 7.24 (d, 1H), 5.38 (dxd, 1H), 4.17, 3.79 (dxd, 2H), 3.48 (dxd, 1H), 3.21 (m, 1H), 3.10 (m, 2H), 2.78 (d, 1H), 1.80 (4H), 1.44 (S, 9H). IR (KBr): 1771, 1737 cm$^{-1}$.

Example 7

1-Carboxymethyl-3β-phthaloylamino-4β-(2-ethoxycarbonyl) ethan-1-yl-azetidin-2-one A solution of 10.4 g of the compound from Example 3 was treated with 85 mL of trifluoroacetic acid in methylene chloride (140 mL, 0° C.). All volatiles were removed at 0° to −15° C., after reaction completion (6 h at 0° C.). Diethylether (50 mL) was added and the mixture filtered to afford the title compound, (8.30 g, 92%).
m.p. 140°–144° C.
MS (FD), m/z 375 (M+1, 100%)
Analysis Calculated for C$_{18}$H$_{18}$N$_2$O$_7$: Calc.: C, 57.75; H, 4.84; Found: C, 57.61; H, 5.00; C, 57.56; H, 4.79.
$[\alpha]_D$= +5.44°,+5.87° (C=1 methanol)
$[\alpha]_{365}$= −24.97°, −25.4° (C=1, methanol)
HPLC (Zorbax ® C-8, 254 nm)>99%

$^{13}$C NMR (CDCl$_3$):δ14.04, 23.61, 30.74, 42.16, 56.99, 58.60, 123.90, 131.60, 134.67, 165.27, 167.48, 170.95, 172.37.

$^1$H NMR (CDCl$_3$):δ2.65 (1H, broad s), 7.90 (m, 2H), 7.80 (2H, m), 5.50 (d, 1H), 4.05 (q, 2H), 1.17 (t, 3H).

Example 8

1-(Carboxymethyl)pyrrolidinate-3β-(2-pyrrolidinocarbonyl) benzoylamino-4β-(2-ethoxycarbonyl)ethan-1-yl To a solution of the compound from Example 7 (8.00 g) in tetrahydrofuran (80 mL) was added pyrrolidine (3.3 mL). After completion (25° C., 2.3 h) of the reaction all solvent was removed under vacuum to afford the title compound as a foam (11.03 g); this compound was used in Example 9 without further purification.

HPLC Analysis (Zorbax® C-8, 254 nm) showed 98.8% integration, partial reversion to phthalimide.

Example 9

Disodium-1-(carboxylate)methyl-3β-(2-pyrrolidinocarbonyl)benzoylamino-4β-(2-carboxylate)ethan-1-yl-azetidin-2-one The title compound from Example 8 (1.00 g) was dissolved in tetrahydrofuran-water (60 mL, 5:1 v/v) and treated with sodium hydroxide (1.000N, 3.88 mL added in 5 portions over 2.0 h; 25° C.). HPLC (Zorbax® C-8, 254 nm buffer: methanol-water 1.0:1.85 with 0.05M ammonium acetate) analysis indicated 88–90% yield of desired product. All solvent was removed in vacuo and the foam was triturated with ether to afford the title compound (830 mg, 85%).

[α]$_D$ = +8.36° (C=1, methanol)
[α]$_{365}$ = +35.61° (C=1, methanol)
HPLC, 85% integration.
$^1$H NMR (DMSO-d$_6$):δ 9.23 (1H, NH), 7.2–7.8 (4H, aromatic), 5.20 (1H).
MS (FAB) m/z=462.

Example 10

1-carboxymethyl-3β-(2-pyrrolidinocarbonyl)benzoylamino-4β-(2-carboxy)ethan-1-yl-azetidin-2-one A 9.74 g sample of the compound of Example 8 was dissolved in tetrahydrofuran-water (510 mL, 7.5:1. v/v, 25° C.) and sodium hydroxide (18.9 mL of 1N) was added (3 min) followed by an equal second portion (over 2 h). During the course of this addition (1 h) acetonitrile (100 mL) was added. When the reaction was complete, solid carbon dioxide was added followed by hydrochloric acid (37.7 mL of 1N, pH=4.0). The aqueous phase was saturated with sodium chloride and was extracted with ethyl acetate-methylene chloride (1:1, v/v, 7×200 mL) after which the dried organic layer (sodium sulfate and 4Å molecular sieves) was evaporated (6.5 g, hygroscopic white foam). Before use this material was triturated with ether and vacuum dried).

HPLC (Zorbax®RX, 254 nm) 72% integration.

Example 11

Diphenyl 1-(carboxylate)methyl-3β-(2-pyrrolidino-carbonyl)benzoylamino-4β-(2-carboxylate)ethan-1-yl-azetidin-2-one Treatment of the diacid (2.41 g) from Example 10 with a mixture of phenol (2.1 equiv), 4-dimethylaminopyridine (0.2 equiv.) with dicyclohexylcarbodimide (2.50 g) in methylene chloride-dimethylformamide (20 mL, 1:1 v/v) provided 3.29 g of impure diphenyl ester. Preparative liquid chromatography employing step elution with ethyl acetate/hexane afforded the title compound.

TLC: Rf, 0.55 (ethyl acetate-hexane, 1:1).
$^{13}$C NMR (CDC13):6 carbonyls at 171.36, 169.7, 168.0, 166.6, 166.5. Aromatic carbons at 150.6, 150.1, 136.6, 131.6, 131.4, 129.6, 129.5, 129.4, 129.3, 126.5, 126.31, 125.9, 121.6, 121.3.
IR (CHCl$_3$): 3400 (weak), 1760, 1664, 1218 cm$^{-1}$.
$^1$H NMR (CDCl$_3$):δ8.05 (d, 1H), 7.91 (d, 1H), 7.00 to 7.60 (m, 13H), 5.53 (dxd, 1H, cis), 4.55 (d, 1H), 4.23 (m, 2H), 4.12 (d, 1H), 3.6–3.8 (m, 2H), 3.12 to 3.27 (m, 2H), 2.58 to 2.75 (m, 2H), 2.09 to 2.3 (m, 1H), 1.80 to 2.11 (m, 5H).
MS(FD) m/z=569 (M+100%).

Example 12

1-(p-Nitrobenzylcarboxylate)methyl-3β-(2-pyrrolidinocarbonyl)benzoylamino-4β-(2-phenylcarboxylate)-ethan-1-yl-azetidin-2-one To solution of the diester (169 mg) from Example 11 in p-nitrobenzyl alcohol in tetrahydrofuran (20 mL) was added sodium tert-butoxide (0,645M in tetrahydrofuran, 0.020 mL added in 6 portions at −10° to −20° C. over 18 h). Acetic acid (2 βL) was added and all solvent removed in vacuo. Chromatography over silica gel (20 g, gradient elution with ethyl acetate-hexane-methanol) afforded 161 mg (80%) of the title compound as a solid foam.

MS (FD) m/z=628 (M+).
TLC: Rf, 0.28 (ethyl acetate-hexane, 1:1).
$^1$H NMR (CDCl$_3$):δ 8.33 (d, 2H), 8.17 (d, 1H), 7.83 (d, 1H), 7.13 to 7.55 (m, 8H), 6.98 (d,2H), 5.43 (dxd, 1H), 5.21 (2H, s), 4.30 (d, 1H), 4.11 (m, 1H), 3.86 (d, 1H), 3.50 to 3.78 (m, 2H), 3.17 (m, 2H), 2.40 to 2.70 (m, 2H), 2.01 to 2.17 (m, 1H), 1.86 to 1.99 (m, 5H).

Example 13 p-Nitrobenzyl-7β-(2-pyrrolidinocarbonyl)benzoylamino-1-carba(dethia)-3-hydroxy-3-cephem-4-carboxylate To a solution of sodium tert-butoxide in tetrahydrofuran (0.59 mL, 0.68M, ≦ −70° C.) was added the diester (50 mg) prepared in Example 12 which was dissolved in 1.0 mL of tetrahydrofuran which had been precooled to ≦ −70° C. After which (total of 3 min at −78° C.) the solution was poured onto ice (25 g) and washed with hydrochloric acid (2N, 25 mL). The aqueous phase was back extracted (methylene chloride, 50 mL) after which the combined organic extracts were dried over sodium sulfate and evaporated. The product (white foam) was triturated with t-butyl methyl ether (about 0.1 mL) and purified by silica gel chromatography (ethyl acetate, toluene, acetic acid, 4:7:1).

STLC: Rf 0.36; integration >95% (260 run)
[α]$_{365}$ = +246° (C=0.05, methanol)
MS (FD), m/z=534 (100%).
$^1$H NMR (CDCl$_3$, overlays with above example):
CD (EtOH), [θ]$_{280}$ = +6500, [θ]$_{232}$=0; [θ]$_{217}$= −13,750

PREPARATION 2 p-Nitrobenzyl 7β[phthalisoimido]-1-carba(dethia)-3-chloro-3-cephem-4-carboxylate To a stirred mixture of p-nitrobenzyl 7β-amino-1-carba(1-dethia)-3-chloro-3-cephem-4-carboxylate (10 g), methylene chloride (1 L), water (50 mL), and sodium bicarbonate (5.98 g) was added phthaloyl dichloride (5.00 mL) at 5°-7° C. over 20 min. After stirring 45 min, methanol was added (15 min, 5°-7° C.) followed by acetic acid (pH 7, 1.62 g). At 5° C. the organic layer was washed (50 mL 50% brine, 50 mL of saturated brine), dried (10 g, 4Å molecular sieves, 20 min), and evaporated to an oil (16 g). Addition of 100 mL of ether prompted crystallization of the title compound (10.15 g, 80%). A second crop was collected from 50 mL ether (2.639 g, total yield >90%)

TLC: Rf, streak to 0.4 ( ethyl acetate-hexane, 1:1) m.p. 140°-145° C. (decomposes).

IR (CHCl$_3$) 1777, 1735, 1705 cm$^{-1}$ (No—OH or —NH).

$[\alpha]_D^{25} = -156.6°$ (C=1, CHCl$_3$) UV (EtOH), λ(E): 266 (21400), 215(27600).

$^{13}$C NMR (CDCl$_3$): δ 6 22.72, 31.97, 52.49, 66.21, 66.38, 123.37, 123.63, 123.77, 125.57, 128.23, 128.84, 130.65, 130.70, 133.58, 135.61, 142.39, 147.84, 152.08, 160.18, 163.72, 164.08.

MS (FD) m/z=481.5 (M+), 483.5 (M++2)

$^1$H NMR (Acetone-d$_6$):δ 5.67 (d, H), 5.48 (dxd, 2H) 4.18 (dxd), 2.23 (m, 2H).

PREPARATION 3 p-Nitrobenzyl-7β-phthaloylamino-1-carba(dethia)-3-chloro-3-cephem-4-carboxylate

A mixture of p-nitrobenzyl 7β-[2-[(1-pyrrolidino)carbonyl]phenyl]carbonylamino-1-carba(1-dethia)-3-chloro-3-cephem-4-carboxylate (2.00 g) dissolved in tetrahydrofuran-water (10:1 v/v, 22 mL) containing boric acid (2.0 g) and hydrofluoric acid (48%, 1 mL) was allowed to react (25° C., 96 h) after which additional hydrofluoric acid (1 mL) and boric acid (2 g) were added. After stirring (25° C., 5 min.) the first crop of product was collected and in a like manner a second crop was collected (after 24 h, 25° C.). The filtrate was evaporated in vacuo and starting material recovered (1.1 g, 55%) after trituration with water (30 mL), filtration, and drying. The combined first and second crops of product were purified by chromatography (40 g silica, elution with 40% ethyl acetate in methylene chloride) affording the title compound (700 mg, >90% based on recovered starting material).

HPLC: (Zorbax® C-8, 254 nm) 96.9% integration corrected for solvent absorbance.

IR(CHCl$_3$) 1726, 1387 cm$^{-1}$.

m.p. 186°-191° C.

MS (FD), m/z 481.

$^{13}$C NMR(CDCl$_3$): δ 21.76, 31.90, 53.14, 56.91, 66.33, 123.50, 123.76, 123.97, 128.95, 130.25, 131.47, 134.82, 142.32, 147.87, 160.02, 161.02, 167.35.

$^1$H NMR(CDCl$_3$, partial):δ 5.53 (1H, d) 5.43 (dxd, 2H), 4.03 (1H, m), 2.69 (m, 2H) UV (ethanol)λ(E) 272 (19300), 243 (15100), 220 (45600).

$[\alpha]_D^{25} = -37.5°$ (C=1, CHCl$_3$)

PREPARATION 4 p-nitrobenzyl-7β-phthaloylamino-1-carba(dethia)-3-chloro-3-cephem-4-carboxylate

To a solution of triphenylphosphite (0.1 mL) in methylene chloride (1.0 mL, −30° C.) was added a slight excess of chlorine (<5 min). Excess chlorine was discharged with amylenes and this solution was added to p-nitrobenzyl-7β-(2-pyrrolidinocarbonyl)benzoylamino-1-carba(dethia-3-hydroxy-3-cephem-4-carboxylate in ethyl acetate (1.0 mL) and pyrimidine (0.025 mL, −40° C.). Additional solvent (2 mL, methylene chloride) was added and the mixture was warmed (−20° C., 0.5 h; 0° C., 1 h; 25° C., 2 h). After which, the mixture was quenched with water (1 mL, 25° C., 1h). Analysis by HPLC indicated about 68% of 3-chlorophthalimide admixed with about 32% of 3-chloro-orthopyrrolidinocarbonylbenzamide (acyl-protected-3-chloro) (total yield estimated from HPLC=60%). The above extracts were washed with hydrochloric acid (0.1N, 2×1 mL), water (2×1 ml) and dried with sodium sulfate. Evaporation of solvents and purification (preparative thin layer chromatography, ethyl acetate-toluene-acetic acid, 4:7:1) afforded the title compound.

MS (FD) m/z 480.7 (M+) 482 7 (M+2, 35%

$^1$H NMR, TLC; and HPLC were identical to the example above (derived in turn from material prepared according to the reference of Bodurow, et al., Tetrahedron Lett. 1989, 30, 2321).

PREPARATION 5

7β-Phthaloylamino-1-carba(dethia)-3-chloro-3-cephem-4-carboxylic acid

A solution of the p-nitrobenzyl ester (155 mg) from Preparation 4 was hydrogenated (1 atm, 25° C. 2.5 h) in tetrahydrofuran-acetic acid-water (5:1:0.075, 6 mL) with palladium on carbon (5% w/w, 8.2 mg). After filtration, the solvent was removed in a nitrogen stream and the residue dissolved in ethyl acetate (75 mL). Normal extractive work-up involving washing (3×25 mL of 0.1N HCl ), back-extraction (25 ml ethyl acetate), drying (4A molecular sieves), and solvent evaporation afforded the acid (120 mg, 100%).

$[\alpha]_D^{25} = -33.5°$ (C=1, methanol)

UV (EtOH): A(E), 221, (40800), 263 (10900)

MS (FD) m/z =346 m.p. 230-234° C. (decomposition)

HPLC (Zorbax®RX, 254 nm) 99.6% integration

IR (KBr) 3183, 1768, 1729 cm$^{-1}$

TLC: Rf, 0.27 (Toluene-ethyl acetate-acetic acid, 5:5:1)

Analysis Calculated for C$_{16}$H$_{11}$ClN$_2$O$_5$: Calc.: C, 55.43; H, 3.20; N, 8.08; O, 23.07; Cl, 10.23. Found: C, 55.67; H, 3.36; N, 7.89; O, 23.19; Cl, 10.07.

Example 14 p-Nitrobenzyl 7β-(2-pyrrolidinocarbonyl)benzoyl-amino-1-carba(dethia)-3-chloro-3-cephem-4-carboxylate The isoimide (7.50 g) from Preparation 2 was dissolved in tetrahydrofuran (−12° C.) and treated with pyrrolidine (1.30 mL, −10° C. to −14° C., 45 min). All volatiles were removed in vacuo, dry ether (125 mL) was added, and the title compound collected by filtration (8.03 g, 93% after drying).

$[\alpha]_{589} = -8.67°$ (C=1, CHCl$_3$).

IR (CHCl$_3$) 3400 (weak, NH), 1778, 1735 cm$^{-1}$.

MS 553.5 (M+1, 100%) 48.4 (M+ - pyrrolidine)

HPLC: (Zorbax®RX, 254 nm) 96.9% integration $^1$H NMR (CDCl$_3$): δ 8.23 (d, 2H), 8.21 (d, 1H), 5.61 (dxd, 1H) 5.38 (dxd, 2H), 3.86 (m, 1H), 2.63 (m, 2H)

$^{13}$C NMR (CDCl$_3$) δ carbonyls at 160.13, 165.18, 167.62, 169.8 m.p. 120°-125° C. TLC: Rf, 0.42 (ethyl acetate - toluene-acetic acid, 4:7:1).

Example 15

1-t-Butoxycarbonyl-3δ-(2-(R)-1-p-nitrophenylethyl aminocarbonyl)benzoylamino-4β-(1,1-dimethoxy)prop-2-ene-3-yl azetidin-2-one A 110 mg sample of 1-t-butoxycarbonylmethyl-3β-phthaloyl-4β-(1,1-dimethoxy)prop-2-ene-3-yl-azetidin-2-one (and 3,4,α, α isomer mixture) and (R)-1-para-nitrophenylethylamine (50 mg) were allowed to react in tetrahydrofuran (1.00 mL, 25° C., 8 d) after which the soluent was removed in vacuo and the acetal isolated by extractive work-up with ethyl acetate, hydrochloric acid (0.1N), and sodium bicarbonate. Solvent evaporation provided 154 mg (100%) of the title compound.
TLC: Rf, 0.68 (10:10:1 ethyl acetate, hexane, methanol)
UV (EtOH) λ (ε) 271 (11000).
MS (FD) m/z=596.
Analysis Calculated for $C_{30}H_{36}N_4O_9$: Calc.: C, 60.39; H, 6.08; N, 9.39; Found: C, 60.17; H, 6.08; N, 9.13.
$^1$H NMR (CDCl$_3$, partial) :δ 8.18 (d, 2H), 7.87 (d, 0.5H), 7.83 (d, 0.5H), 3.28, 3.26, 3.24, 3.23 (four s, 1.5 H each ), 1.49, 1.46 ( 2 s, 4.5 H each ).
$^{13}$C NMR (CDCl$_3$):δ carbonyls 169.8, 169.4, 168.0, 167.7, 166.6.

Example 16

1-(2,4-dimethoxybenzyl)-3β-2-(S-(+)-2-methoxy-methylpyrrolidinocarbonyl)benzoylamino-4β-(2-phenyl)-ethene-1-yl-azetidin-2-one A solution of 1-(2,4-dimethoxyphenyl)-3β-phthaloyl-4β-(2-phenyl)ethene-1-yl-azetidin-2-one(and 3,4,α, α isomer mixture) (2.34 g), S-(+)-2-methoxymethyl pyrrolidine (0.69 g), dimethylformamide/tetrahydrofuran (1:1, 10 mL) was allowed to react (25° C., 7 d) after which all solvent was removed in a stream of nitrogen (25° C., 1 d). Vacuum drying produced a foam (2.9 g, 100%), 98% pure by HPLC.
UV ( EtOH ) λ 251 (ε=20,000)
$[\alpha]_D^{25°} = -36.39°$, $[\alpha]_{365} = -152.35°$ (C=1, methanol)
MS (FD) m/z=583 (M+). 469,354.
$^{13}$C NMR (DMSO-d$_6$): δ 55.12, 55.4 (diasteromeric methyls of methoxy methylpyrrolidineamide, 1:1)
TLC: Rf, 0.23 (ethyl acetate-toluene-acetic acid, 7:4:1)
IR (CHCl$_3$): 1753, 1720 absent ( present in phthalimido starting material), 1665 ( amide ), 3438 (weak NH).
$^1$H NMR (DMSO-d$_6$): δ 9.15 (two d, 0.5 ea), 5.37 (two dxd, 0.5 H ea) 3.28 (S, 1.5H), 3.32 (1.5H).

Example 17

1-(2,4-dimethoxybenzyl)-3-phthaloylamino-4-(2-phenyl)-ethene-1-yl-azetidin-2-one A solution of (mixture of 1:1 cis-β-lactam diastereomers, 500 mg from example 16), boric acid (195 mg), hydrofluoric acid (187 mg), tetrahydrofuran-water (9:1, 13 mL) were allowed to react at 25° C. Progress of the reaction was followed by HPLC on a Zorbax®RX column with methanol-water-triethylamineammonium acetate (2400 mL:1200 mL: 40 mL:30 g, then pH to 6 with acetic acid) at 0.5 mL/min at 254 nm (slow reacting isomer =35 min, fast reacting isomer =43 min, phthalimide product =49 min). After 120 h, HPLC analysis suggested about a 10:1 ratio of slow/fast reacting isomers and about 65% conversion into the corresponding phthalimide product. All solvent was removed in vacuo and methylene chloride was added. Extractive work-up involving water, aqueous sodium bicarbonate and drying (sodium sulfate) afforded a white foam. A portion (400 mg) of this material was purified by chromatography on silica (toluene-ethyl acetateacetic acid 10:4:1) affording the slow reacting isomer. (This intermediate contained about 9% of the fast reacting isomer (average as calculated from $^1$H NMR and HPLC assay data).
$^1$H NMR (CDCl$_3$):δ 5.63 (d, 1H), 5.38 (dxd) 7.6 to 8.3 (mx, 8H), 4.03 (1H, m), 2.71 (m, 2H), 2.20 (mx, 2H).

I claim:

1. A compound of the formula

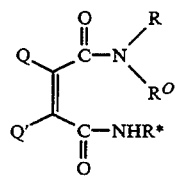

wherein R* is a group of the formula

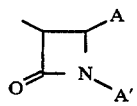

wherein R and R$^0$ are individually C$_1$-C$_6$ alkyl groups or together form a ring consisting of the nitrogen atom to which they are attached and two to seven carbon atoms, said ring optionally substituted by one or more C$_1$-C$_6$ alkyl and/or C$_1$-C$_6$ substituted alkyl groups;

Q and Q' are individually hydrogen, C$_1$-C$_6$ alkyl, or when taken together form a divalent radical of the formula —CH=CH—CH=CH—;

A and A' together form a group of the formula

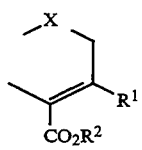

wherein R$^2$ is hydrogen or a carboxy-protecting group;
X is —CH$_2$—;
R$^1$ is hydrogen, hydroxy, halo, C$_1$-C$_6$ alkoxy, C$_1$-C$_6$ alkyl, C$_1$-C$_6$ substituted alkyl, C$_1$-C$_6$ alkylthio, C$_1$-C$_6$ substituted alkylthio, C$_7$-C$_{12}$ phenylalkyl, C$_7$-C$_{12}$ substituted phenylalkyl, phenyl or substituted phenyl; a group of the formula

—COR$^3$ wherein R$^3$ is hydrogen, C$_1$-C$_6$ alkyl, C$_1$-C$_6$ substituted alkyl, C$_7$-C$_{12}$ phenylalkyl, C$_7$-C$_{12}$ substituted phenylalkul, phenyl, substituted phenyl, amino, (monosubstituted)-amino, or (disubstituted)-amino; a group of the formula

—COOR$^4$ wherein R$^4$ is hydrogen, or a carboxy-protecting group.

2. A compound of claim 1, wherein the —NRR$^0$ group is pyrrolidino.

3. A compound of claim 1 which is

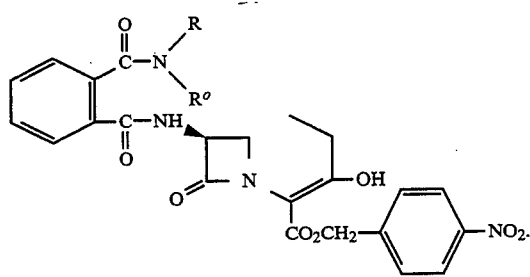
4. A compound of claim 3 wherein the group —NRR⁰ is pyrrolidino.
* * * * *

UNITED STATES PATENT AND TRADEMARK OFFICE
CERTIFICATE OF CORRECTION

Page 1 of 2

PATENT NO. : 5,391,728
DATED : February 21, 1995
INVENTOR(S) : Leland Weigel

It is certified that error appears in the above-identified patent and that said Letters Patent is hereby corrected as shown below:

Column 25 structure should read as shown on attached page--.

Signed and Sealed this

Twenty-first Day of November, 1995

*Attest:*

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,391,728

DATED : February 21, 1995

INVENTOR(S) : Leland Weigel

It is certified that an error appears in the above-identified patent and that said Letters Patent is hereby corrected as shown below:

reading-- " 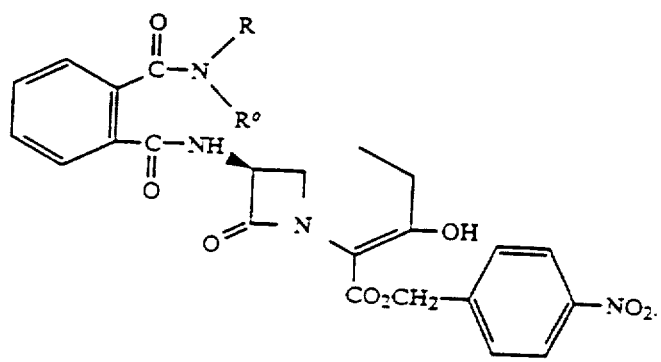 "

should read -- 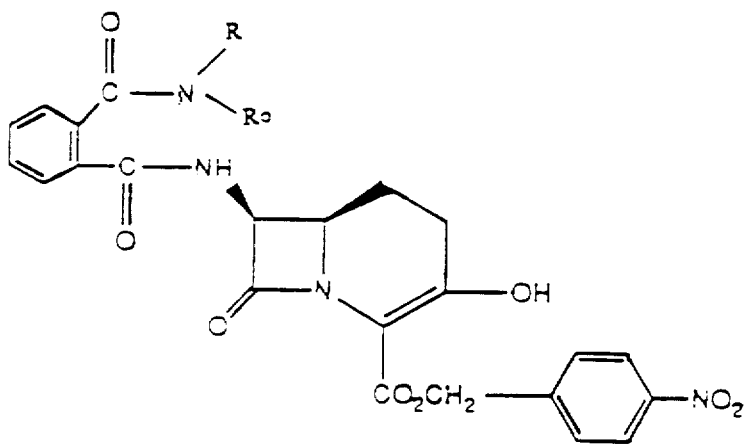 --.